United States Patent [19]

Ikegami et al.

[11] 3,988,530
[45] Oct. 26, 1976

[54] AUTOMATIC DEFECT-DETECTING METHOD AND APPARATUS

[75] Inventors: Yoshizo Ikegami; Kuniomi Abe; Seijiro Kushibe, all of Kobe; Takao Yoshinaga, Kawanishi; Tsunemasa Okada, Kobe, all of Japan

[73] Assignees: Konan Camera Research Institute; Sumitomo Metal Industries, Ltd., Japan

[22] Filed: Sept. 30, 1975

[21] Appl. No.: 618,263

[30] Foreign Application Priority Data
Oct. 2, 1974 Japan............................ 49-114144

[52] U.S. Cl................................. 178/6; 178/6.8; 178/DIG. 36; 178/DIG. 37; 250/562; 356/199
[51] Int. Cl.².................................. H04N 7/19
[58] Field of Search................. 178/6.8, DIG. 37, 6, 178/DIG. 36; 250/562, 563; 356/199

[56] References Cited
UNITED STATES PATENTS

| | | | |
|---|---|---|---|
| 2,798,605 | 7/1957 | Richards | 178/DIG. 37 |
| 2,803,755 | 8/1957 | Milford | 178/DIG. 37 |
| 3,019,347 | 1/1962 | Laycak | 178/DIG. 37 |
| 3,020,034 | 2/1962 | Laycak | 178/DIG. 37 |
| 3,379,829 | 9/1968 | Gambrell | 178/DIG. 37 |
| 3,889,053 | 6/1975 | Lloyd et al. | 178/6 |

*Primary Examiner*—Robert L. Griffin
*Assistant Examiner*—Edward L. Coles
*Attorney, Agent, or Firm*—Wenderoth, Lind & Ponack

[57] ABSTRACT

An automatic surface defect-detecting method and apparatus for detecting only effective significant surface defects. The significant defects can be detected from video signals and differential signals corresponding to particular scanning lines respectively by removing the distributed density portions having a larger pulse width in the scanning line direction, or removing smaller differential value portions in density, from the examined portions with higher density of flourescent magnetic powders thereon.

5 Claims, 9 Drawing Figures

AUTOMATIC DEFECT-DETECTING METHOD AND APPARATUS

The present invention relates to a magnetic powder defect-detecting method and more particularly to an automatic defect-detecting method and apparatus which can determine or detect the existence of any defects on the surface of an examined object such as a billet or plastic plate of long length by processing the scanning signals from scanning the examined object, which has fluorescent magnetic powder attached thereon, with a television camera or a photo-multiplier.

A magnetic powder defect-detecting method for examining an object is known. Some methods have been proposed to detect the defects in the examined article having fluorescent magnetic powder thereon by scanning operations with the use of television cameras, etc.

Generally, in detecting defects on the surface of an examined object by these known methods, it is very difficult to process the video signals of a television camera, since the examined objects are not always clean, or some defects are only mere scratches, not defects which it is desired to detect. Thus, a sysem has been proposed to detect the defects on the examined object by addressing the video signals of a television camera in order to store each signal. In this system, it is difficult to pick up signals indicative of significant defects, due to the enormous amount of information and complicated processing circuits needed therefor.

These problems have become large hurdles in automation of a process of defect-detection and marking, since these problems become serious in actuating a marking apparatus in response to a defect detection signal, the marking apparatus providing a mark at each defect to indicate the location of the defect upon detection of the defect.

In recent years, color-emitting magnetic powders have been developed. The fluorescent magnetic powders are colored by applying a liquid, with a color former contained therein, to the flourescent magnetic powders to color any area of the surface of the object on which a defect has been detected, so that the defects can be made visible to the naked eyes. Accordingly, markings are not always required to be effected by correctly memorizing the length and breadth of the portions of the article surface containing the defect as before. If the existence of the defects in a given range can be detected positively, it is possible for the existence of the defects to be confirmed easily by scattering or applying the liquid to the range of the surface of the article.

The present invention is provided in response to the development of the color-emitting fluorescent magnetic powders. It is the primary object of the present invention to provide an automatic defect detecting method and apparatus which can pick up signals indicative of significant defects more easily and accurately as compared with the conventional defect-detecting systems, and furthermore is suitable for effecting the markings of the defect containing portions of the articles being examined.

Therefore, it is an object of the present invention to provide an automatic defect-detecting method which can pick up only the signals indicative of significant defects of the use of scanning signals corresponding to particular scanning lines of a television camera, etc. by automatically removing, in a signal processing stage, signals indicative of defects such as oil stains, fine defects, etc.

The particular scanning lines are scanning lines of a particular order in the case of a face scanning type television camera, and scanning lines themselves in case of a line scanning type television camera and a photo-multiplier.

Accordingly, in the present invention, it is a fundamental requirement to remove any wider signals caused by the oil stains, etc. by cutting out the wider signals. Any signals, which are at a given level or higher, are picked up from the scanning signals corresponding to particular scanning lines and are cut out when the pulse width of the picked-up signals is wider than a predetermined value. On the other hand, in the case of fine linear defects, etc., it is a fundamental requirement to detect the existence of the defects to be marked by differentiating the video signals and to cut out the signals which are at a given level or lower from the differential signals, and then to produce a logical sum of the scanning signals of the predetermined width or smaller and differential signals of the predetermined level or higher.

A second object of the present invention is to provide a retaining circuit to prevent the omission of the detection of defects on a single scanning line, the retaining circuit being adapted to transmit a defect-indicating signal of, at least, the one particular scannine line even when no defect-existing signal is present in the scanning operation of at least the one particular scanning line if the defect-existing signal is obtained by the scanning operation before and after the scanning of, at least, one particular scanning line, while the existence of the defects is checked sequentially through the particular scanning lines.

A third object of the present invention is to provide an automatic defect-detecting apparatus equipped with a defect width decision circuit, the defect width decision circuit being provided with a kind of addressing effect by omitting unnecessary pulse width decisions, the differential signals of the given level or higher being used as trigger pulses for a circuit for deciding the width and narrowness of each pulse of the scanning signals, the width and narrowness of the pulse being adapted to be decided only when the pulse with a large differential value, in other words, with a sharp inclination, is present.

A fourth object of the present invention is to provide an automatic defect-detecting method and apparatus by which a defect signal is transmitted to a marking apparatus after deciding whether or not the defect is to be marked, when a given number of defect-indicating signals or more are continued, or the defect-indicating signals are continued, except for at least one signal among the sequence of signals, from the existence and absence of the defects corresponding to particular scanning lines.

In accordance with the objects set forth above, the present invention provides an automatic defect-detecting method and apparatus comprising a retaining circuit which prevents omission of any detection of defects on a single scanning line, a defect width deciding circuit which omits unnecessary pulse width decisions and has a kind of addressing effect, and a defect-detecting circuit which transmits defect signals for carrying out marking.

Additional objects, advantages, and characteristic features of the present invention will become readily apparent from the following detailed description of one preferred embodiment of the invention when taken in conjunction with the accompanying drawings, wherein.

Figure 1:
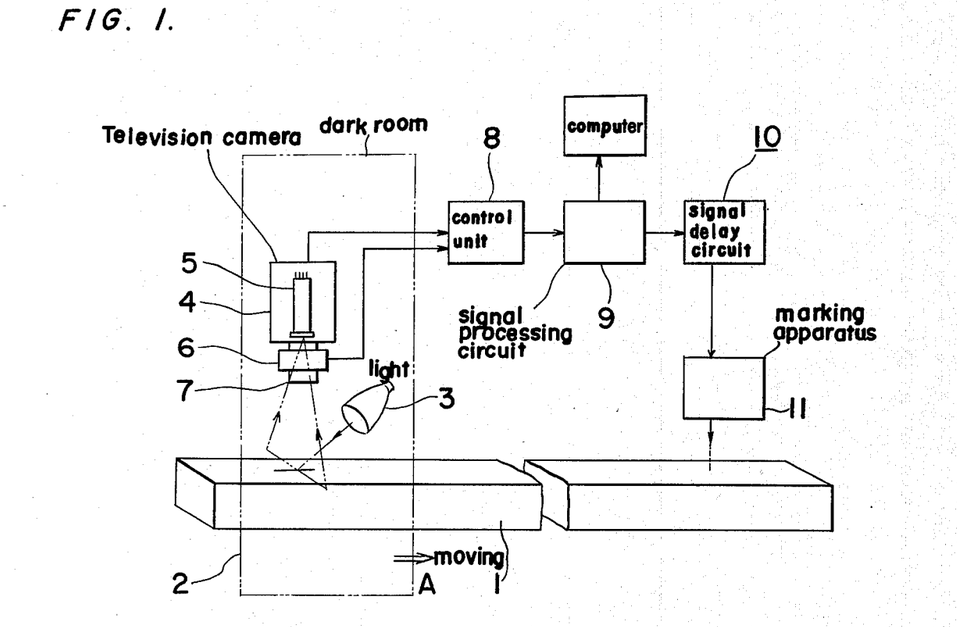
FIG. 1 is a block diagram showing the entire system for defect signal processing in accordance with the present invention.

Referring to FIG. 1 showing the entire system of the automatic defect-detecting apparatus, an examined article 1 is moved in one direction A, for instance, at a constant speed, the examined article such as a billet or plastic material, etc. having color emitting fluorescent magnetic powder on the surface thereof. A dark room 2 is preferably provided and indicated diagramatically in the drawing. A light source 3 applies ultraviolet rays to the surface of the examined material 1 from a given direction in the dark room 2. A television camera 4 is mounted above the examined material 1 located in the dark room 2, the television camera having a camera lens system 5 directed downwardly, and a known picture receiving tube 6 incorporated therein. An optical filter 7 allows only light rays each having a wave length effective to detect the surface defects to pass through the optical filter, the light rays being selected from among reflected light rays from the examined material 1. A television camera control unit 8 controls the scanning operation of the television camera 4, and selects and transmits only the video signals corresponding to particular scanning lines. A signal processing circuit 9 transmits a defect-existing signal when the video signals from the television camera control unit 8 have been processed and a defect to be marked has been detected. A signal delay circuit 10 transmits an operation signal after a given delay time from the time the defect existing signal from the signal processing circuit 9 has been transmitted. The operation of a marking apparatus 11 is controlled by the operation signal of the signal delay circuit 10 and places markings on the portions of the object 1 where defects have been detected.

Figure 2:
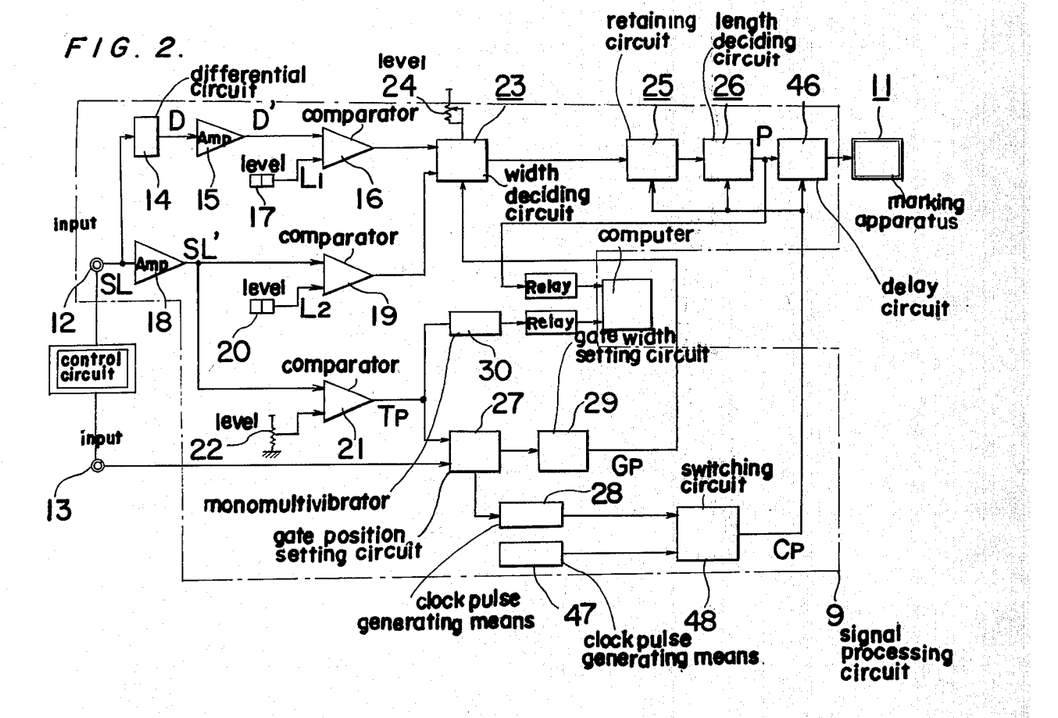
FIG. 2 is a block circuit diagram showing one specific example of a signal processing circuit in accordance with the present invention.

Referring to FIG. 2 showing the basic construction of the signal processing circuit 9, numeral 12 is the input terminal for a video signal SL for the particular scanning line-selected from the television camera control unit 8, and numeral 13 is the input terminal 13 for the synchronizing signal thereof. A differentiation circuit 14 differentiates the video signal SL and transmits a differentiation signal D. An amplifier 15 amplifies the differentiation signal D. A first comparator 16 compares a differentiation signal D' from the amplifier 15 with a digitally set given level L1 from a slice level means 17 (later described) connected thereto and transmits the differentiation signal D' only when the differentiation signal D' is larger than the given level L1.

An amplifier 18 amplifies the video signal SL as it is. A second comparator 19 receives video signals SL' properly amplified by means of the amplifier 18, and transmits only a video signals SL' larger than the given level L2 which is set by another slice level means 20 connected thereto. A third comparator 21 connected to the amplifier 18 receives the amplified video signal SL' and transmits the video signal SL' when it is higher than a trigger level LT determined by a trigger level means 22 connected thereto and employing a veriable resistance, etc. for detecting the edges of the examined material 1.

A defect width deciding circuit 23 decides whether the defect is a significant defect by simultaneous impression thereon of the output of the first comparator 16 and the output of the second comparator 19, namely from the differentiation signal D' of the video signal SL and the pulse width of the video signal SL. A defect width setting means 24 provides a defect width standard.

Figures 3, 4, 5:
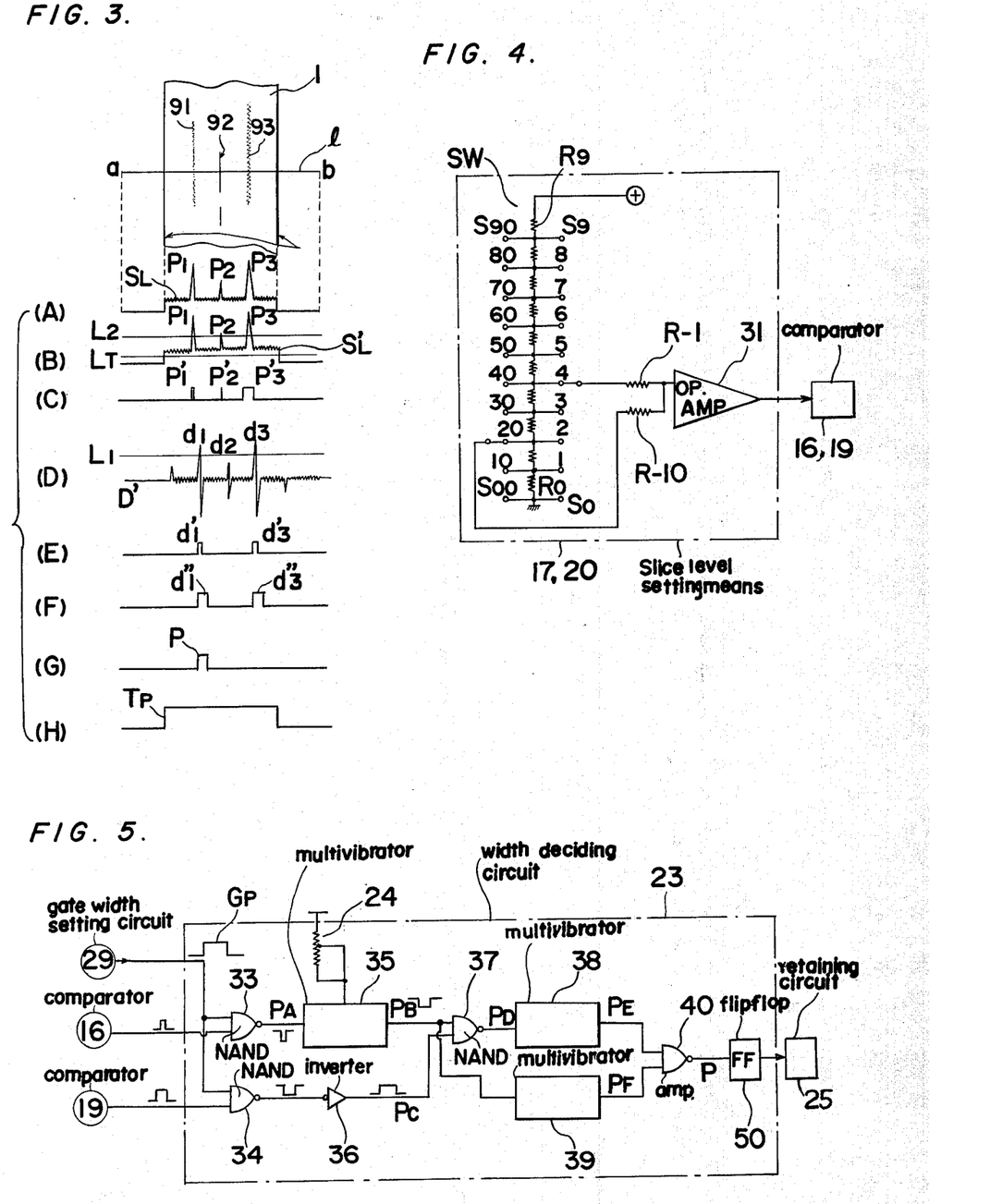
FIG. 3 is a pulse wave form chart for illustrating the fundamental principle of the defect signal processing in accordance with the present invention.
FIG. 4 is a diagram showing one example of slice level setting means in accordance with the present invention.
FIG. 5 is a block circuit diagram showing one example of a defect width deciding circuit in accordance with the present invention.

As shown in FIG. 3, as the television camera scans the examined material 1 across a range between a and b larger than the width of the examined material 1, the video signal SL corresponding to a particular scanning line l has, for example, a wave form SL as shown in part (A) of FIG. 3 in response to the surface condition of the examined material 1.

It will be assumed that the surface of the examined material 1 has portions 91, 92 and 93 each having a high density of fluorescent magnetic powder thereon, and that the portion 91 represents a significant defect which it is desired to detect, and the portions 92 and 93 are portions, respectively, which are not significant and which are not desired to be detected as a defect, the portion 92 being a mere fine-line-like scratch, a portion 93 being a stain of oil, or something.

One portion of the video signal SL, which has three peaks P1, P2 and P3 corresponding to portions 91, 92 and 93, is differentiated by a differentiation circuit 14 as described hereinbefore. The one portion of the video signal SL is impressed upon the first comparator 16 as a differentiation signal D' which has been amplified by the amplifier 15. The first comparator compares a given slice level L1, which is set by the slice level means 17, with the differentiation signal D' as shown in part (D) of FIG. 3, and only pulses d1 and d3 having differentiation values larger than the slice level L1 are produced as output from the comparator.

The video signal SL is amplified by means of the amplifier 18 and then is supplied the second comparator 19 and the third comparator 21. As shown in FIG. 3, (B), the second comparator 19 produces as output pulses P1, and P2 and P3, which are larger than the slice level L2 set by the slice level means 20. The third comparator 21 detects a time at which the video signal SL' becames larger, for the first time, in response to the edge of the examined material 1, than the trigger level LT set by the trigger level means 22 and produces a trigger pulse TP as shown in FIG. 3, (H).

The defect width deciding circuit 23 first changes the wave form of the outputs d1 and d3 of the first comparator 16, from among the respective outputs of the first comparator 16 and the second comparator 19, into rectangular pulses d1″ and d3″ each having a given pulse width as shown in FIG. 3, (F), and then changes the wave form of the outputs P1, P2 and P3 of the second comparator 19 into rectangular pulses P1′, P2′ and P3′ each having a pulse width proportional to the respective pulse width of the pulses P1, P2 and P3, as shown in FIG. 3, (C). The rectangular wave P2′ among these waves P1′, P2′ and P3′ is removed by comparision of the rectangular waves P1′ and P3′ with rectangular waves d1″ and d3″ triggered by the pulses d1′ and d2′ shown in FIG. 3, (F). The rectangular wave P3′, which is larger than a reference defect width predetermined by the defect width setting means 24, is removed from among the compared rectangular waves P1′ and P3′. As shown in FIG. 3, only (G), a defect indicating pulse P, which meets conditions for a defect which it is desired to detect, is finally produced from width deciding circuit 23.

Referring back to FIG. 2, a retaining circuit is connected to width deciding circuit 24. When a defect indicating pulse has been obtained in the preceding and succeeding scanning operation relative to a particular scanning line, the retaining circuit 25 continuously retains any defect indicating pulse from the preceding scanning line and from the next succeeding scanning line, if no defect indicating pulse is obtained in the scanning operation of a particular scanning line. The retaining circuit is provided to prevent actual defects from being overlooked. If a defect is discontinued slightly in the direction of advance of the examined material 1, a defect-indicating pulse may be produced again in the next scanning operation.

When a defect fails to produce a defect indicating signal once, it cannot be decided that the defect exists no longer. Therefore, defect length deciding circuit 26 is provided which produces a defect indicating signal P indicating an actual defect when a defect-indicating pulse P′ has been supplied through the retaining circuit 25 several times continuously.

A gate position setting circuit 27 delays for a proper delay time a synchronous signal from input terminal in response to a trigger pulse Tp supplied thereto by the third comparator 21. A clock pulse generating circuit 28 connected to gate position setting circuit 27 generates internal clock pulses, after a proper delay time, from the synchronous signal supplied through the gate position setting circuit 27. A gate width setting circuit 29 connected to the gate position setting circuit sets a given gate width in response to the output of the gate position setting circuit 27, and impresses the gate output upon the defect width deciding circuit 23. A clock pulse Cp from an internal clock pulse generating means 28 or an external clock pulse generating means 47 is selectively impressed, by means of a clock switching circuit 48, upon the retaining circuit 25, the defect deciding circuit 26 and the delay circuit 46 (later described).

A monomultivibrator 30, connected to the third comparator 21, increases the pulse width of the trigger pulse Tp to a pulse width twice the period of the trigger pulse Tp, and impresses, upon a control system such as a computer, etc. (indicated schematically), a signal indicating the existence and absence of the material 1, namely, a signal indicating the existence of the material 1 to be inspected.

Construction of certain essential circuits among the circuits constituting the signal processing circuit 9 will be described hereinafter.

The slice level setting means elements 17 and 20, is shown in FIG. 4 and is a digital switch SW having terminals corresponding to unit and tens figures constituted by connecting, in series, ten (in total) resistors R0 to R9 each having the same resistance value and providing two contacts at each connecting point. The output voltage of any one of the contacts S0 to S9 on the side of the unit number terminals is supplied, through a resistor R-1, to a voltage amplifier 31, and the output voltage of any of the contacts S00, S10, ..., S90 of the tens terminals is supplied to the voltage amplifier 31 through a resistor R-10 having a resistance value one tenth that of the resistor R-1 corresponding to the units contacts, and is added to the output voltage from the width contacts.

The output of the voltage amplifier 31 is supplied to the first comparator 16 or the second comparator 19 as a slice level L1 or a slice level L2, respectively, as described hereinabove.

As shown in FIG. 5, the defect width deciding circuit 23 is composed of a NAND gate 33 receiving the output of circuit 29 and the differentiation output signal (see FIG. 3, (E)) from the first comparator 16; a NAND gate 34 receiving the output of the gate width setting circuit and the output signal (see FIG. 3, (C)) corresponded to the video signal SL of the second comparator 19; a one shot multivibrator 35, to which the NAND output PA of the NAND gate 33 is supplied thereby to produce a defect width setting pulse PB having a given pulse width predetermined by a defect width setting means 24; an inverter 36 to which the NAND output of the NAND gate 34 is supplied and which produces an inverted output DC; and NAND gate 37 to which the outputs of the multivibrator 35 and the inverter 36 are connected for producing a logical sum PD of the output pulse PB of the one shot multivibrator 35 and the defect width pulse PC inverted by the inverter 36; a one shot multivibrator 38 connected to the output of NAND gate 37 for producing an output pulse PE at the fall of the output pulse PD of the NAND gate 37; a one shot multivibrator 39 connected to the output of multivibrator 35 for producing an output pulse PF at the rise of the output pulse PB; and a NAND gate 40 connected to the outputs of multivibrators 38 and 39 for obtaining the logical sum of the output pulses PE and PF of the one shot multivibrators 38 and 39.

In the defect width deciding circuit 23, each NAND gate 33, 34, 37 and 40 can be replaced by an AND gate.

Figure 6:
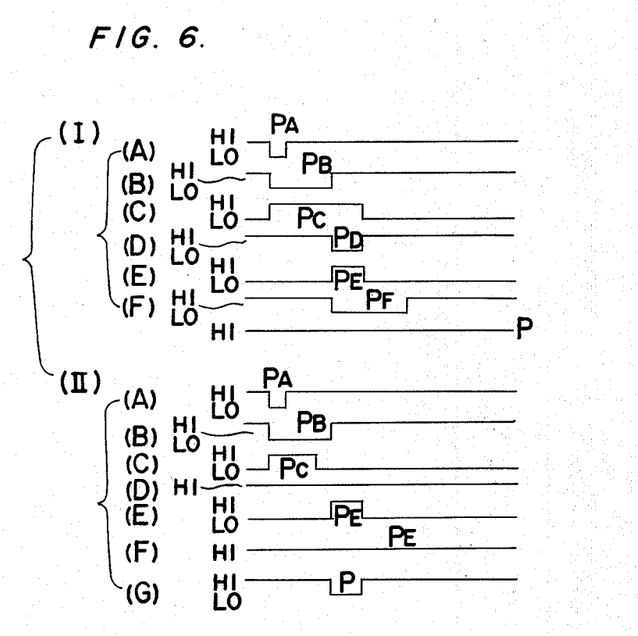
FIG. 6 illustrates the operation of the defect width deciding circuit shown in FIG. 5, parts (I) and (II) showing pulse wave form charts, respectively, for a defect width signal larger than the predetermined width, and a defect width signal smaller than the predetermined width.

Operation of the defect width deciding circuit 23 as described hereinabove will be described hereinafter. As shown in FIG. 6, (I) (B) and (II) (B), the defect width setting pulse PB having a pulse width predetermined by the defect width setting means 24 is produced by the one shot multivibrator 35 upon the fall of an output pulse PA, which was supplied through the NAND gate 33 from the first comparator 16. The defect width setting pulse PB and the defect width pule PC, shown in FIG. 8 (I) (C) and (II) (C), are logically combined in the NAND gate 37, the defect width pulse PC passing through the NAND gate 34 and the inverter 36.

When the defect width pulse PC has a larger pulse width than the defect width setting pulse PB, the output PD from the NAND gate 37 is a pulse as shown in FIG. 6, (I) (D). The one shot multivibrator 38 operates due to the fall of the output pulse PD to transmit a gate input pulse PE as shown in FIG. 6 (I) (E). The other one shot multivibrator 39 produces an output pulse PF shown in FIG. 6 (I) (F) due to the rise of the defect setting pulse PB. When the NAND combination of these pulses PE and PF is obtained from NAND gate 40, the output P of the NAND gate 40 remains at HI, since one input is LO and the other is HI. Accordingly, the defect width pulse PC which has a large defect width is removed.

When the pulse width of the defect width pulse PC is smaller than the pulse width of the defect width setting pulse PB, the NAND combination of the pulses PB and PC is at HI, and the gate input pulse PE remains HI as shown in FIG. 6, (II) (E). On the other hand, the one shot multivibrator 39 operates due to the rise of the defect width setting pulse PB thereby to transmit a pulse PF shown in FIG. 6, (II) (F). Accordingly, the NAND gate 40 produces an output pulse P at level LO correspondingly while both PE and PF are HI. The LO output pulse P shows the existence of the video signal which is greater than a set differentiation value, and which lies within a given defect width. It is referred to as a defect-indicating signal hereinafter.

The defect width decision is effected every time differentiated defect-indicating signals d1'' and d2'' are supplied.

The defect-indicating signal P is supplied to the retaining circuit 25 through a flip-flop 50.

Figure 7:
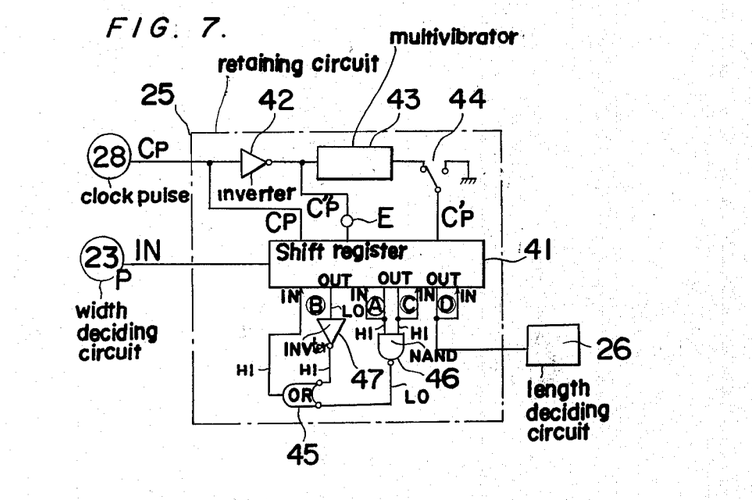
FIG. 7 is a block circuit diagram showing one example of a retaining circuit in accordance with the present invention.

As shown in FIG. 7, the retaining circuit 25 is composed of a shift register 41 of the 4-bit parallel input-parallel output type at the center of the retaining circuit. As a clock pulse for shifting of the shift register 41, either the clock pulse CP of the internal clock pulse generating means 28 or the clock pulse CP of the external clock pulse generating means 47 corresponded to the feeding of the examined material 1 is selectively used by a clock switching circuit 48. As a clock pulse for presetting, the output pulse CP' of a one shot multivibrator 43, which operates due to the fall of voltage after the clock pulse Cp has been inverted by means of an inverter 42, is used. The clock pulse Cp' for presetting is impressed upon the shift register 41 through a change-over switch 44.

These clock pulses CP and CP' are impressed respectively upon the shift register 41 by a switching means shown in E of the diagram. When the clock pulse to be impressed through the inverter 42 is LO, the clock pulse CP for shifting is selected. When the clock pulse is HI, the clock pulse CP' for presetting is selected. The output of a first stage A and of a third stage C of the shifter register 41 are supplied to a NAND gate 46. The output of a second stage B is supplied to an OR gate 45 through an inverter 47. Also, the output of the NAND gate 46 is supplied directly to the OR gate 45. The output of the OR gate 45 is supplied to the second stage B.

Operation of the retaining circuit 25 as described hereinabove will be described hereinafter.

Figure 8:
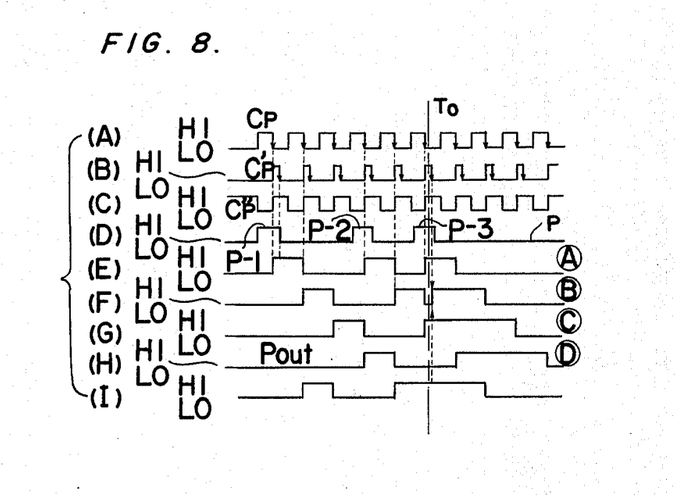
FIG. 8 is a pulse wave form chart illustrating the operation of the retaining circuit shown in FIG. 7.

As shown in FIG. 8, it is assumed that defect-indicating signals P-1, P-2 and P-3 are supplied to the shift register 41, at first, at intervals of two time periods, and then, at intervals of one time period. When the defect-indicating signal P is supplied at intervals of two time periods, a first defect-indicating signal P-1 is shifted sequentially from the first stage A to the second stage B, and to the third stage C as shown in parts (E), (F), (G) and (H) of FIG. 8 and is produced as output from a fourth stage D. In effecting the shifts of the first defect-indicating signal P-1, the signal P-1 is preset at each time the shift proceeds. The next defect-indicating signal P-2 passes through the second stage B from the first stage A and is shifted to the third stage C. As a third defect-indicating signal P-3 is supplied to the first stage A, an HI signal is supplied to the second stage B through the NAND gate 43 and the OR gate 45. The HI signal (see FIG. 8, (I)) is preset in the second stage B due to fall of the clock pulse cp' for presetting. The HI condition is provided from the first stage A to the third stage C. A continuous defect-indicating signal Pout is supplied from the fourth stage D as shown in FIG. 8, (H).

Assuming that the retaining circuit 25 of FIG. 7 is now in the condition To shown in FIG. 8, the output signals from the stages A, B and C are in the states of HI, LO and HI, respectively. How these states are obtained can be easily understood by simply shifting the obtained original signal P. The output signals from the stages A and C, which are both in the HI state, are supplied to the NAND gate 46, and the output signal from the NAND gate 46, which is in the LO state, is supplied to the OR gate 45. In the meantime, the output signal from the stage B, which is in the LO state is inverted to the HI state by the inverter 47, and then is supplied to the OR gate 45. Consequently, the OR gate 45 produces a signal in the HI state which is fed back to the input of the stage B. Therefore, the pulse wave in the stage B becomes HI, after the moment To. FIG. 8 (I) shows the waveform of the signal after having been preset in the state B and which is to be shifted to the stage C, while FIG. 8 (F) shows a waveform of the signal before having been preset in the stage B.

Figure 9:
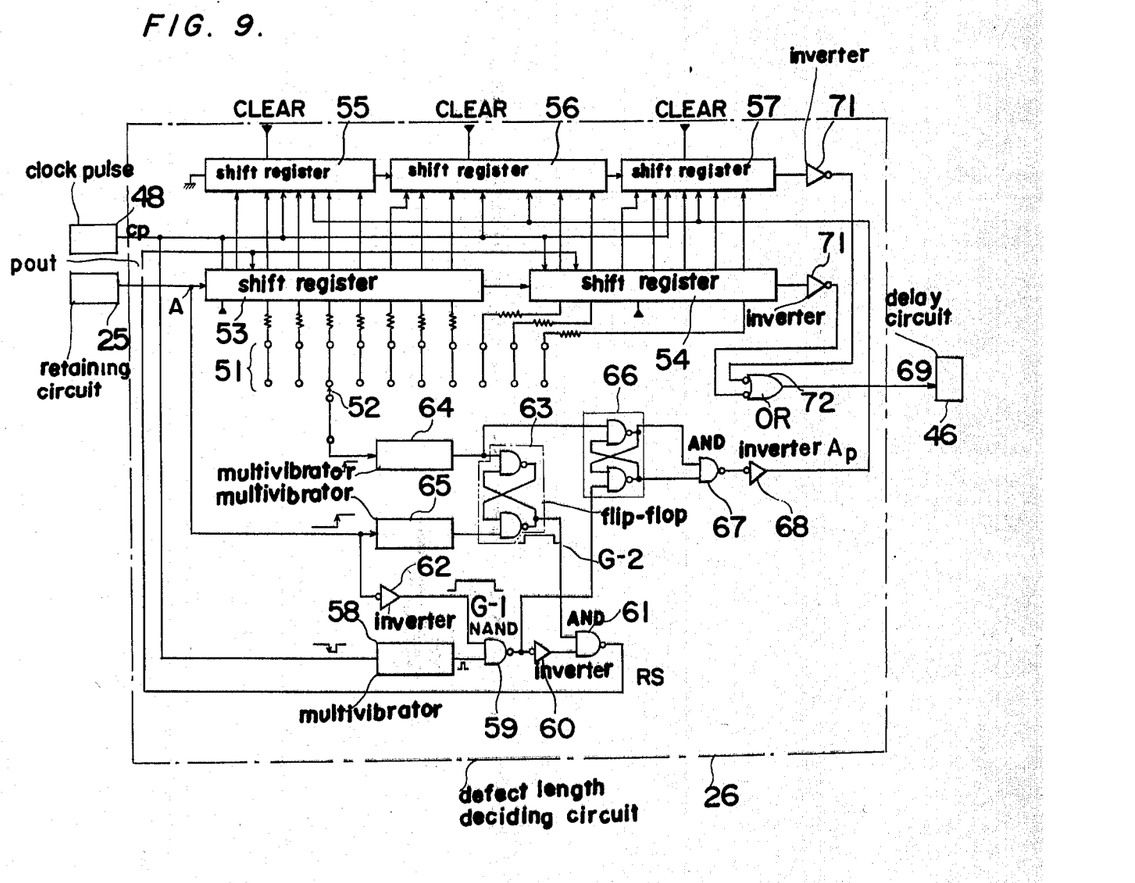
FIG. 9 is a circuit diagram showing one example of a defect length deciding circuit in accordance with the present invention.

The output of the retaining circuit 25, namely, the defect-indicating signal Pout is supplied to the defect length deciding circuit 26 as shown in FIG. 9.

The defect length deciding circuit 26 decides the length of the defect in numbers of the length divided in a synchronizing signal unit. Namely, assume that the feeding speed of the material 1 being examined is, for example, 18 m per minute, and the examined material 1 advances 5 mm every synchronizing unit (for example, one sixtieth sec.). Accordingly, a defect 10 mm long corresponds to two synchronizing unit. A defect 30 mm long will give rise to to six continuous defect indicating signals Pout, like wise. Accordingly, it is assumed that a defect of, for example, 20 mm long or more is to be detected in practice. The reference frequency of four is set by a switch 52 forming part of a panel 51. If the defect produces a succession of defect-indicating pulses above the set reference frequency, it is determined to be a defect which is to be detected. A defect signal corresponded to the actual length of the defect is then produced. When the defect produces a succession of defect indicating pulses below the set reference frequency, a defect signal is not produced.

Referring to FIG. 9, a defect indicating signal Pout is supplied to two series connected shift-registers 53 and 54, and the defect indicating signal Pout is sequentially shifted by the clock pulse CP.

In this case, the switch 52 of the panel 51 is connected to the fourth stage of the shift register 53. The reference frequency is thus set at four.

An output from each state of the shift registers 53 and 54 is connected to the input of the respective stages of three series connected shift registers 55, 56 and 57 connected in parallel with shift registers 53 and 54.

The defect length deciding circuit 26 operates in two different ways, in relation to the pulse width of the signal Pout provided from the retaining circuit 25. The first operation is for clearing the shift registers 53 and 54. This operation occurs when the signal Pout is smaller than four bits, for example three bits. When the three bit signal Pout shifts through the shift register 53, the trailing edge of the signal Pout passes a common junction A before the leading edge of the signal Pout reaches the fourth stage. In other words the three bit signal Pout is completely included in the shift register 53 between the common junction A and the fourth stage. Therefore, the signals applied to the multivibrators 64 and 65 will never become HI at the same time.

The shift registers 53 and 54 are reset by a resetting signal (described later), due to the fact that the defect indicating signal Pout is contained within the first four stages of shift register 43.

The clear signal RS for the shift registers 53 and 54 is produced between the shifts in response to the fall of the clock pulse CP by a one shot multivibrator 58 upon which the clock pulse CP is impressed. The clear signal RS is supplied to an AND gate 59. The output of the AND gate 59 is supplied through an inverter 60 to an AND gate 61.

The defect-indicating signal Pout is inverted, by an inverter 62 and thereafter is supplied as one gate signal G-1 to the AND gate 59.

The output of a flip-flop 63 is supplied to the other AND gate 61 as the gate signal G-2 therefor. In the flip-flop 63 the output of a fourth stage of the shift register 53 from the switch 52 corresponding to the set reference frequency is supplied as one-way input through a one shot multivibrator 64 which operates upon the input to change it from LO to HI, and the defect indicating signal Pout is supplied as other-way input through another one shot multivibrator 65.

As described above, since the signals applied to the multivibrators 64 and 65 do not become HI at the same time, the input thereto is LO when the defect indicating signal Pout is contained in the first four stages of the shift register 53, so that the gate signals G-1 and G-2 open the gate 59 and the gate 61 to impress the clear signals RS from one shot multivibrator 58 upon the shift registers 53 and 54, respectively, to clear them. The second operation is for supplying the signal Pout from the shift registers 53 and 54 to the shift registers 55, 56 and 57. This operation occurs when the signal Pout is greater than or equal to four bits, for example five bits. When the five bit signal Pout shifts through the shift register 53, the trailing edge of the signal Pout is still behind the common junction A after the leading edge of the same reaches the fourth stage. Therefore, the signals to be applied on the multivibrators 64 and 65 can both be in HI state at the same time.

The flip-flop 63 is thus reset. At the time of resetting of the flip-flop 63, the output of the one shot multivibrator 64 is LO. Thus, a flip-flop 66 which is connected to the output of multivibrator 64 is due to the change of the output of multivibrator 64 from HI LO, and becomes resettable. The output of the one shot multivibrator 58 for clearing is supplied through the AND gate 59 as the other input to the flip-flop 66. Accordingly, both outputs of the flip-flop 66 are impressed, respectively, upon each shift register 55, 56 and 57, as presetting signals Ap, through an AND gate 67 and an inverter 68. The state of the shift registers 53 and 54 are preset upon each shift register 55, 56 and 57.

Upon advancing of the input through the shift registers, the flip-flop 66 is reset. Each shift register 55, 56 and 57 becomes shiftable and is shifted by a clock pulse CP. A defect signal P having a defect length, which is proportional to the frequency of the continuous defect indicating signal Pout, is generated at output end 69.

The output of the shift register 54 and the output of the shift register 57 are supplied on an OR gate 72 respectively through inverters 70 and 71. This is because the output is provided directly to the output end 69 from the shift register 54 until the presetting of the shift registers 55, 56 is carried out and 57 when HI signals not less than the number of total bits of the shift registers 53 and 54 are supplied.

In the defect length decided circuit 26, the defect signal P corresponding to the length of the defect is obtained. Pulses proportional to the length of the defect are generated by means of a pulse generator by counting the continuous repetitions of the defect indicating signals Pout and converting the number counted into the defect length.

The defect signal P obtained as described hereinabove is supplied to a delay circuit 46 as shown in FIG. 2. The delay circuit 46 delays the defect signal P for a required time. When the defect reaches a position adjacent the marking apparatus in order to be marked, the defect signal P is supplied to the marking apparatus 11, which has a known construction, at a time suitable for operating the marking apparatus 11. Upon supplying of the defect signal at the proper time, the marking apparatus 11 sprays a developer on the portion of the surface of the material having the defect thereon to color-develop the defect, the developer used being one for the color-forming fluorescent magentic powder on the defect-containing portion of the surface, and furthermore sprays a fixing solution on the color developed portion to fix the color.

In the embodiment, this differentiation signal output of the first comparator 16 is used as a trigger for the defect width deciding circuit 23. In principle, the invention need not be so limited. A logical sum of the differentiation signal output, which has a differentiation value larger than a given level, and a video signal, which has a pulse width equal to a given pulse width or less, may be used.

Also, the levels or values to be set in the first comparator 16, the second comparator 19, the defect deciding circuit 23, the defect length deciding circuit 6, etc. may be varied in accordance with the condition of the defects characteristic of the examined material 1. The particular value thereof is not required to be kept constant.

Furthermore, the structure of the defect width deciding circuit 23, the retaining circuit 25, etc. may be varied within the scope of the present invention, and is not limited to the construction described.

Thus, according to the present invention, the video signals are not required to be addressed as they are conventionally. The present invention provides a method and apparatus in which effective defect indicating signals can be obtained extremely easily by determining the scanning line width and the differentiation values of the high density portion of fluorescent magnetic powder.

Furthermore, in the present invention, even when the defect indicating signal for a series of scanning lines is interrupted, at least one time, the defect indicating signal is continued if a defect indicating signal is produced again, so that the accuracy of detection can be improved, without depending upon the addressing system, by detecting even a defect which is likely to be overlooked in a prior art defect detecting method using this type of fluorescent magnetic powders.

Also, in the automatic defect detecting apparatus in accordance with the present invention, when the differentiation signal having a given differentiation value or greater is used as the trigger for the defect width deciding circuit, the distributed density portion which is not sharp relative to the defect indicating portions can be removed in advance, and unnecessary decisions are to the defect width can be avoided, whereby the detection accuracy can be improved.

In addition a television camera of an area scanning type can be employed in the embodiment, but the scanning signals can be processed by the method and apparatus for the present invention by line scannings at given times by a television camera of the line scanning type or a photo-multiplier, etc., whereby the defects can be detected.

As many apparently widely difference embodiments of this invention may be made without departing from the spirit and scope thereof, it is to be understood that the invention is not limited to the specific embodiment thereof except as defined in the appended claims.

What is claimed is:

1. In a defect detecting method for detecting defects in the surface of a material to be examined by scanning the surface of the examined material having a fluorescent magnetic powder thereon by a means for producing a scanning signal having a level of strength corresponding to the concentration of the fluorescent powder on the scanned surface, the automatic defect detecting method comprising the step of picking up said scanning signal for each of a series of adjacent scanning lines and comparing the scanning signal with a predetermined pulse width from among the thus obtained signal pulses for producing first defect indicating signals, the step of differentiating the scanning signals corresponding to said scanning lines and comparing the differentiation signal with a predetermined level to obtain signal pulses above the given level for producing second defect indicating signals, and the step of producing the logical sum of said first defect indicating signals and said second defect indicating signals for corresponding scanning lines, whereby the existence or absence of the defects on particular scanning lines can be detected by existence and absence of the logical sum signals.

2. An automatic defect detecting method according to claim 1 further comprising the step of retaining the logical sum signal corresponding to one particular scanning line at least until the scanning of the next particular scanning line is completed, whereby the existence of a defect to be marked can be detected when the logical sum signal continues for a predetermined number of turns in succession.

3. In a defect detecting apparatus for detecting defects in the surface of a material to be examined by scanning the surface of the examined material having a fluorescent magnetic powder thereon by a means for producing a scanning signal having a level of strength corresponding to the concentration of the fluorescent powder on the scanning surface, an automatic defect detecting apparatus for detecting the existence and absence of defects along a particular scanning line comprising a first comparison circuit for comparing the scanning signal for a particular scanning line with a given level, and producing signals corresponding to the portions of the scanning signal higher than said level, a differentiation circuit for differentiating said scanning signal and producing a differentiated signal, a second comparison circuit coupled to said first comparison circuit and said differentiation circuit for comparing said differentiated signal with a further given level, and producing signals corresponding to the portions of said differentiation signal higher than said further given level, and a defect width deciding circuit coupled to said first and second comparison circuits for producing output signals in response to the output signal of said second comparison circuit when the pulse width of the output signal of said first comparison circuit is smaller than a given pulse width.

4. An automatic defect detecting apparatus according to claim 3 further comprising a retaining circuit coupled to said defect width deciding circuit for retaining the output signal corresponding to at least one scanning line when an output signal from the defect width deciding circuit is present for the immediately preceding and immediately succeeding scanning lines, and producing the retained output signal as a defect indicating signal corresponding to the one scanning line, even when no defect indicating signal exists in the scanning of said one scanning line.

5. An automatic defect detecting apparatus according to claim 3 further comprising a length deciding circuit for adding the output signals from said defect width deciding circuit produced continuously and sequentially from successive scanning lines and produces a signal for defects to be marked when the number of the output signals becomes greater than a given number.

* * * * *